United States Patent
Donitzky

(10) Patent No.: US 7,998,135 B2
(45) Date of Patent: Aug. 16, 2011

(54) DEVICE AND METHOD FOR OPHTHALMOLOGICALLY TREATING THE EYE USING A FIXATION LIGHT BEAM

(75) Inventor: Christof Donitzky, Eckental (DE)

(73) Assignee: Wavelight Laser Technologie AG (DE)

( * ) Notice: Subject to any disclaimer, the term of this patent is extended or adjusted under 35 U.S.C. 154(b) by 1366 days.

(21) Appl. No.: 11/360,119

(22) Filed: Feb. 22, 2006

(65) Prior Publication Data

US 2006/0142742 A1   Jun. 29, 2006

Related U.S. Application Data

(62) Division of application No. 09/949,254, filed on Sep. 7, 2001, now abandoned.

(51) Int. Cl.
*A61B 18/20* (2006.01)

(52) U.S. Cl. ............ 606/5; 606/4; 606/10; 128/898

(58) Field of Classification Search ............ 606/4–6, 606/10–12; 351/205–212; 128/898
See application file for complete search history.

(56) References Cited

U.S. PATENT DOCUMENTS

| | | | |
|---|---|---|---|
| 4,443,075 A | 4/1984 | Crane | 351/209 |
| 4,973,149 A | 11/1990 | Hutchinson | 351/210 |
| 5,029,220 A | 7/1991 | Juday | 382/6 |
| 5,214,455 A | 5/1993 | Penney et al. | 351/210 |
| 5,520,679 A | 5/1996 | Lin | 606/5 |
| 5,644,642 A | 7/1997 | Kirschbaum | 382/103 |
| 5,777,719 A * | 7/1998 | Williams et al. | 351/212 |
| 6,027,216 A * | 2/2000 | Guyton et al. | 351/200 |
| 6,030,376 A * | 2/2000 | Arashima et al. | 606/4 |
| 6,099,522 A | 8/2000 | Knopp et al. | 606/10 |
| 6,159,202 A * | 12/2000 | Sumiya et al. | 606/4 |
| 6,179,421 B1 * | 1/2001 | Pang | 351/205 |
| 6,238,385 B1 | 5/2001 | Harino et al. | 606/4 |
| 6,271,914 B1 * | 8/2001 | Frey et al. | 356/124 |
| 6,406,473 B1 | 6/2002 | Shimmick et al. | 606/5 |
| 6,439,720 B1 | 8/2002 | Graves et al. | 351/211 |
| 6,793,654 B2 * | 9/2004 | Lemberg | 606/5 |
| 2002/0128634 A1 | 9/2002 | Donitzky et al. | 606/5 |
| 2002/0169441 A1 * | 11/2002 | Lemberg | 606/5 |

(Continued)

FOREIGN PATENT DOCUMENTS

DE   196 18 883 A1   5/1996

(Continued)

OTHER PUBLICATIONS

Pier Giorgio Gobbi, et al., "Automatic Eye Tracker for Excimer Laser Photorefractive Keratectomy," *Supplement to Journal of Refractive Surgery*, vol. 11, May/Jun. 1995, pp. S337-S342.

(Continued)

*Primary Examiner* — Ahmed M Farah
(74) *Attorney, Agent, or Firm* — Lewis and Roca LLP

(57) ABSTRACT

A device for ophthalmologically treating the eye has a treatment laser beam (UV) for ablating parts of the cornea (12) and a fixation light beam (24). A fixation light spot in the vicinity of the fovea (30) and the fovea are imaged by means of a camera (40). This makes it possible to check whether the patient has reliably fixated the fixation light source (22). In addition, the pupil can be recorded and both recordings can be superimposed.

8 Claims, 2 Drawing Sheets

U.S. PATENT DOCUMENTS

2003/0007125 A1* 1/2003 Levine .......................... 351/206
2006/0100677 A1* 5/2006 Blumenkranz et al. ......... 607/89
2007/0030446 A1* 2/2007 Su et al. ........................ 351/205

FOREIGN PATENT DOCUMENTS

| DE | 197 023 335 C1 | 1/1997 |
| EP | 0 770 370 A2 | 10/1996 |
| WO | WO 01/45606 A2 | 6/2001 |

OTHER PUBLICATIONS

Fabrice Manns, et al., "Optical Profilometry of Poly (methylmethacrylate) Surfaces After Reshaping with a Scanning Photorefractive Keratectomy (SPRK) System," *Applied Optics*, vol. 35, No. 19, Jul. 1, 1996, pp. 3338-3346.

\* cited by examiner

DEVICE AND METHOD FOR OPHTHALMOLOGICALLY TREATING THE EYE USING A FIXATION LIGHT BEAM

CROSS-REFERENCE TO RELATED APPLICATIONS

This application is a divisional application of U.S. patent application Ser. No. 09/949,254, filed Sep. 7, 2001, now abandoned which claims priority to PCT Application Serial Number PCT/EP01/00393, filed Jan. 15, 2001, and to German Patent Application Serial Number 100 01 131.4, filed Jan. 13, 2000, which are hereby incorporated by reference as if set forth herein.

BACKGROUND

The invention relates to a device for ophthalmologically treating the eye using at least one treatment laser beam to ablate parts of the cornea and a fixation light beam that is provided to be fixated by the patient.

In photorefractive keratectomy (PRK), an ametropia of the human eye is corrected by partly reshaping the cornea. A special PRK method that is appreciably (gaining importance at the present time is LASIK. In the LASIK method, a lid ("flap") is cut in the cornea and folded back. Then a UV laser beam (normally an excimer laser beam having a wavelength of 193 nm) is directed at the exposed parts (laid bare by the lid) of the cornea in order to remove (to ablate) material at that point. After the desired ablation, the lid is shut again and consolidates with the cornea.

The present invention relates generally to PRK and, particular, the LASIK method.

In the photorefractive ophthalmological method, it is important to position the eye precisely with respect to the laser radiation, in particular the ablation beam, used, i.e. in the case of every laser pulse that impinges on the eye in an ablating manner, the system must "know" precisely the point at which the laser beam impinges on the eye. For this purpose, so-called "eye trackers" are used in the prior art. These are devices with which the respective instantaneous position of the eye can be determined in order to control the laser beam in accordance with said determined position. In this connection, the laser beam is guided, for example by means of a scanner, temporally and spatially over the eye surface to he treated (in the case of LASIK, for example, in the stroma), the temporal and spatial control of the laser spot (focus spot) being such that a desired ablation profile is removed (ablated). In this connection, a so-called fixation light beam has to be used in the prior art. A fixation light source is positioned in such a way that the patient can fixate it visually. The patient is asked to do this. This has the object of arresting the eye as constantly as possible in that the patient fixates uninterruptedly the fixation light source. Since the patient has to recognize the fixation light source in this process, it goes without saying that the fixation light source emits a fixation light beam having wavelengths in the visible range, for example, in the green range.

However, the patient does not generally succeed in fixating the fixation light beam in a completely uninterrupted manner. In the prior art, therefore, the said "eye trackers" are known, i.e. optoelectronic systems, with which movements of the eye can be detected. Such movements occur if the patient (involuntarily) "loses sight", literally, of the fixation light source for a more or less short period of time. If the patient fixates the fixation light source in the ideal way, the fixation light is imaged precisely on the fovea. If, on the other hand, the patient loses sight of the fixation light source, the fixation light is no longer imaged on the fovea, but on another point of the retina, that is to say next to the fovea, to a greater or lesser extent remote from it. The said eye tracker of the prior art, which is assumed herein to be known, detects, for example, movements of the eye by recording the pupil by means of a camera and an image evaluation in which movements of the pupil are detected. The treatment laser beam is then controlled in such a way that such detected eye movements are taken into account and the ablation takes place precisely in accordance with the desired ablation profile despite the eye movements.

SUMMARY

The present invention is based on the insight that, in the event of relative positioning of eye and ablation laser beam, special problems may arise if fixation light is used because the patient does not correctly fixate the fixation light source at all during the stress of the operation or for other reasons. The object of the invention is to provide a remedy in such a situation.

According to the invention, said object is achieved by a camera that records the image of the fixation light on the retina, in particular in the region of the fovea, and the fovea. In the ideal case, the spot of the fixation light is situated precisely on the fovea if the patient fixates the fixation light source correctly. If, on the other hand, the patient does not fixate the fixation light source correctly, the fixation light is not imaged precisely on the fovea but at another point in the retina. This can then be detected with the camera provided according to the invention. The optical imaging elements of said camera are so designed that images are imaged sharply in the retina plane in the region of the fovea with the camera. Consequently, the ophthalmologist can establish before and during the operation whether the patient has "his eye" on the fixation light source as prescribed. This check can also be automated by image processing. In this connection, the camera system is at least approximately sharply focused on the retina surface at the level of the fovea, and an image of the fovea and of the adjacent regions of the retina is recorded. Image processing can then establish whether the spot of the fixation light is situated sufficiently precisely on the fovea or not. If it is established that the patient does not fixate the fixation light source sufficiently precisely, i.e. with sufficiently small deviations (viewed temporally and according to distance), the physician can then draw conclusions from this for the treatment and, if necessary, take measures. The checking of the relative position of the fixation light spot on the retina with respect to the fovea can take place before and/or during the operation.

In accordance with a preferred refinement of the invention, not only is the position of the fixation light spot with respect to the fovea measured and evaluated, but the pupil is also additionally recorded by a camera. Both recordings, that is to say the recording of the fixation light spot and fovea, on the one hand, and the recording of the pupil, on the other hand, are performed with respect to a common, constant axis, for example the fixation light axis. The two images differ therefore in the focusing plane: the imaging of the pupil is offset with respect to the imaging of the fixation light spot and fovea by about the diameter of the eye, that is to say 2 to 3 cm.

The recording of pupil and fovea by the fixation light spot can preferably be superimposed on one another, picture is produced in which, on the one hand, the pupil is imaged and, on the other hand, the fovea and the fixation light spot. This makes it possible not only to check whether the patient has reliably fixated the fixation light source, but also to determine a beneficial central axis for the ablation. If the patient fixates the fixation light source then there appear on the superimposed image explained above the pupil, the fovea (more precisely: the macula lutea) and the fixation light spot, the latter precisely centrally in the fovea. Under ideal conditions, the fixation light spot (and the fovea) is situated centrally in the pupil. Under real conditions, however, the fixation light spot together with fovea is frequently not central with respect to the pupil, i.e. on the superimposed image, the fixation light spot with the fovea is offset with respect to the centre of the pupil. With this finding, the subsequent ablation takes place in a centred manner in accordance with a preferred refinement of the invention with respect to a point that is eccentric with respect to the pupil and that is defined by the centre point of the fixation light spot and fovea (with precise fixation, this is one and the same point).

The two recordings mentioned above, that is to say pupil, on the one hand, and fixation light spot with fovea, on the other hand, can be generated by a single camera if the imaging plane (focus) is varied for the two recordings in the manner of an autofocus effect. This can be done with suitable zoom means periodically in a short time sequence so that the said superimposition image can be produced.

On the other hand, however, it is also possible, and preferred at the present time, to work with two cameras, i.e. a first camera records the pupil and another camera simultaneously records the fovea with the fixation light spot. Both images can be combined and superimposed in a computer, and can be displayed on a display in the superimposed state or fed to an automated image processor in the manner described above.

The cameras used are preferably video cameras, particularly preferably solid-state video cameras, for example CCDs or the like.

In this connection, a camera can preferably be used that is available in any case in the ophthalmological treatment system for the purposes of "eye tracking".

BRIEF DESCRIPTION OF THE DRAWINGS

An exemplary embodiment of the invention is explained in greater detail below by reference to the drawing. In the drawing.

DETAILED DESCRIPTION

Figure 1:
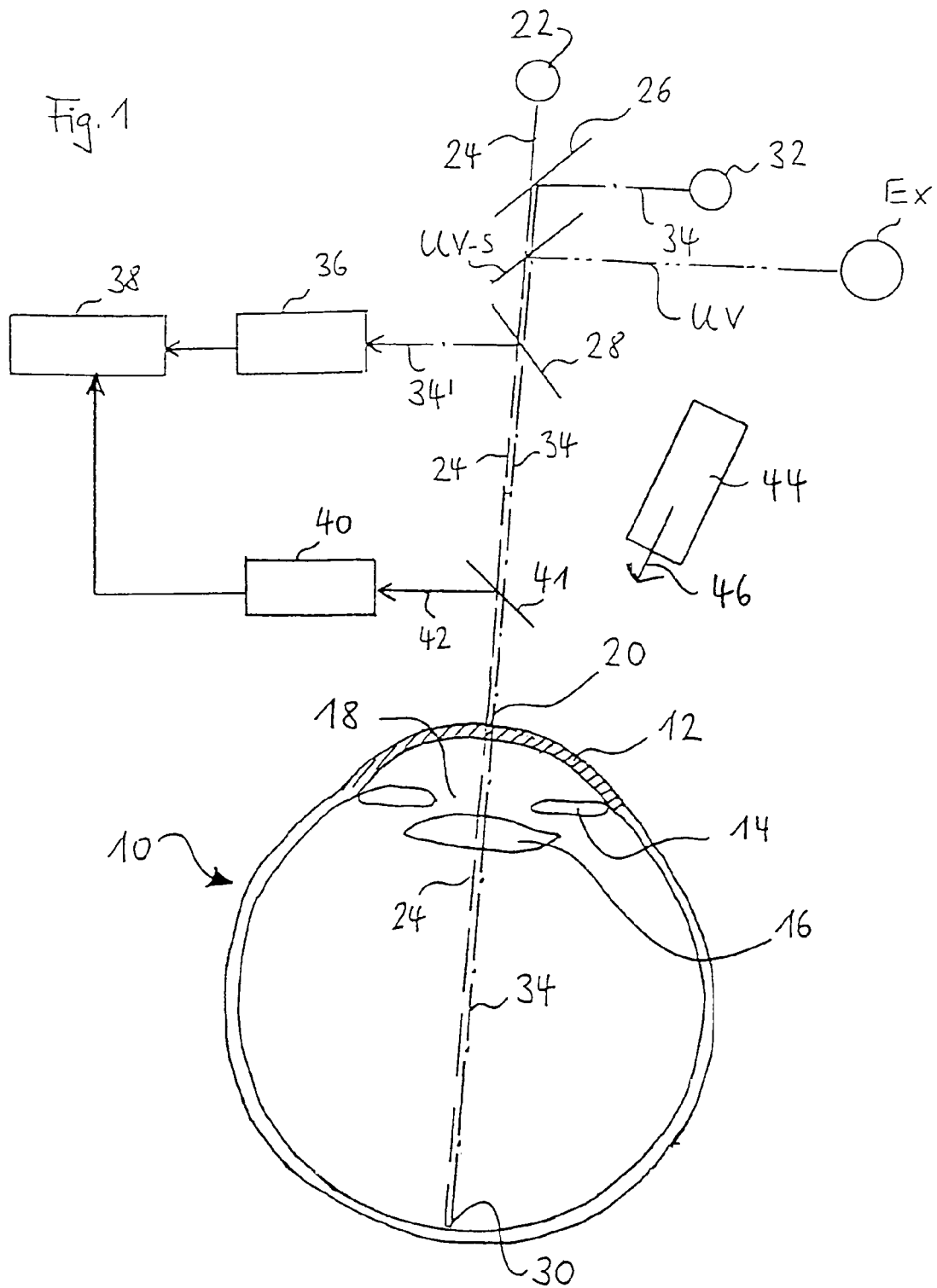
FIG. 1 shows diagrammatically a device for the photorefractive keratectomy of the eye, in particular in accordance with the LASIK method.

The eye 10 shown diagrammatically in FIG. 1 has a cornea 12, an iris 14, a lens 16 and a pupil 18.

A fixation light source 22 known per se emits a fixation light beam 24 that penetrates the front surface of the cornea 12 at the point 20. The wavelength of the fixation light beam 24 is such that it is visible to the patient, that is to say, for example, in the green region of the spectrum. A diode is normally used as fixation light source 22. The fixation light beam 24 is stationary and the patient is urged to fixate the fixation light source, which appears to him to be punctiform.

An excimer laser Ex emits the actual ablation beam, that is to say the beam with which the cornea 12 is reshaped. Said ablation beam UV (for example, 193 nm) is deflected via a mirror UV-S and guided over the cornea 12 in accordance with an ablation algorithm so that the desired ablation profile is removed. The ablation beam is therefore not stationary. The means for moving ("scanning") the ablation beam are known per se and not shown in greater detail in the figure.

The fixation light beam 24 passes through the cornea and the pupil 18 and is imaged on the fovea 30. It is therefore also described as the "line of sight". Said line of sight therefore joins on the object side the fixation point (that is to say the point of the fixation light source 22) to the centre of the entry pupil. The "entry pupil" is the virtual image of the real pupil that an observer sees on viewing the eye.

The position 20 at which the fixation light beam 24 passes through the front surface of the cornea 12 may be chosen as the centre for the ablation, i.e. the ablation profile in accordance with which the ablation beam UV is guided ("scanned") over the cornea 12 is centred on the point 20 at which the fixation light beam 24 passes through the exposed front surface of the cornea 12. In the LASIK method, the front surface of the cornea is in this context the exposed surface after folding back the so-called lid (flap). In order to determine the penetration point 20 on the cornea 12, a centring light source 32 is used that, in the exemplary embodiment shown, emits a laser beam in the infrared range. Said centring light beam 34 is directed via a partly transparent mirror 26 coaxially with the fixation light beam 24 onto the cornea 12. In the figure, the fixation light beam 24 and the centring light beam 34 are shown in parallel next to one another, but they actually extend coaxially, i.e. on a common central axis. This means that the centring light beam 34, which is stationary during the operation, also passes through the front surface of the cornea 12 at the penetration point 20. In the exemplary embodiment, the centring light beam 34 has a wavelength in the infrared range, for example, in the range from 800 to 1100 nm. It is important that the centring light beam 34 has a wavelength that is different from the wavelength of the fixation light beam 24 so that reflections and images that are generated by both beams can be discriminated from one another, i.e. because of the different wavelengths, it is possible to measure a reflection of the centring light beam 34 at the front surface of the cornea 12 without interference by the fixation light beam. Accordingly, the penetration point 20 is measured by measuring the scattered-light/Fresnel reflection of the centring light beam at the front surface of the cornea. For this purpose, a partly transparent mirror 28 is used that directs the scattered-light/Fresnel reflection 341 of the centring light beam onto a camera 36. The camera 36 is, in the exemplary embodiment shown, also for other reasons part of the device, namely as a so-called "eye-tracking camera" (cf. DE 197 02 335 and the prior art mentioned therein).

The use of a special centring light beam 34 to determine the penetration point 20 of the fixed radiation at the front surface of the cornea has, compared with the use of the fixation light beam 24 for this purpose, the advantage that a relatively high-power reflection not swamped by other images can be evaluated by means of the camera 36 and a downstream evaluation computer 38. The scattered light/Fresnel reflection of the fixation light is also itself swamped by the Purkinje-Sanson image, with the result that this reflection is difficult to evaluate.

The camera 36 and the computer 38 into which the camera measurements are inputted, form a so-called eye-tracking system (cf. the abovementioned prior art). For this purpose, the eye is illuminated with independent radiation, for example IR radiation 46, generated by a light source 44 and the pupil 18 is, for example, measured by means of its rim in order to determine, in particular, the geometrical centre of the pupil (the so-called "centre of gravity of the pupil"). In addition, the system comprising camera 36 and computer 38 now also measures the position of the scattered-light/Fresnel reflection of the centring light beam 34 at the front surface of the cornea 12, i.e. at the position of the penetration point 20. The camera 36 is consequently IR sensitive in the exemplary embodiment shown. Preferably, the system comprising camera 36 and computer 38 determine the relative position between penetration point 20 and geometrical centre ("centre of gravity") of the pupil 18.

In order to check whether the patient fixates the fixation light source 22 (i.e. the fixation light beam 24) sufficiently precisely, a further camera 40 is provided in the exemplary embodiment in accordance with FIG. 1. The camera 40 is, for example, a video camera (CCD) and the image signals are likewise electrically inputted into the computer 38. The optical means (not shown) of the camera 40 are designed in such a way that they record an image in the plane of the fovea 30 of the eye 10. The imaged spot of the fixation light beam 24 is, in the ideal case, i.e. if the patient fixates the fixation light source 22 precisely, situated precisely on the fovea 30. If the fixation on the part of the patient is inaccurate, the fixation light spot is situated alongside the fovea 30. The camera 40 therefore receives via a partly transparent mirror 41 radiation with which the image plane of the fovea and its surroundings is recorded in the camera 40. The image thus produced with fovea and fixation light spot can be displayed to the physician on a viewing screen so that he can check the fixation on the part of the patient. The evaluation of the images can also be automated in the computer 38 using the technology of image processing.

In FIG. 1, the individual laser radiation sources and the deflection mirrors are shown only diagrammatically for the purpose of facility of inspection. In practice, the excimer laser beam will be coupled in a different way to that shown, in particular as near as possible to the eye since special requirements are imposed on partly transparent mirrors for UV radiation. Consequently, the arrangement of the partly transparent mirrors in practice will be such that the mirror UV-S is still underneath the mirror 41.

In accordance with a preferred refinement of the invention, the cameras 36 and 40 shown in FIG. 1 are used (the camera 36 additionally to the function described above) in such a way that an image of the pupil 18 is recorded by the 35 camera 36 and inputted into the computer 38, while the above described image in the plane of the fovea 30 with the fixation light spot on the retina is recorded by the camera 40 and likewise inputted into the computer 38. Both images are recorded with respect to a fixed common axis so that both images can be superimposed on one another in the computer 38, with the result that a conclusion is possible relating to the relative positioning of the fovea, fixation light spot and pupil.

Figure 2:
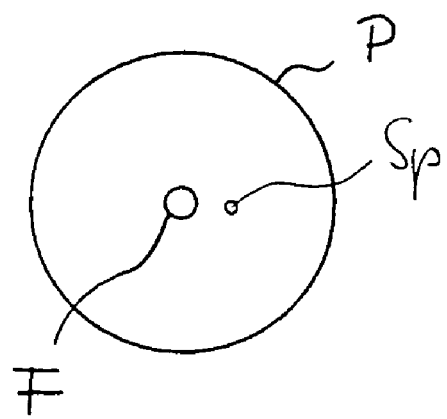
FIGS. 2, 3 and 4 show diagrammatically superimposition images of pupil, fovea and fixation light spot in various situations.
Figure 3:
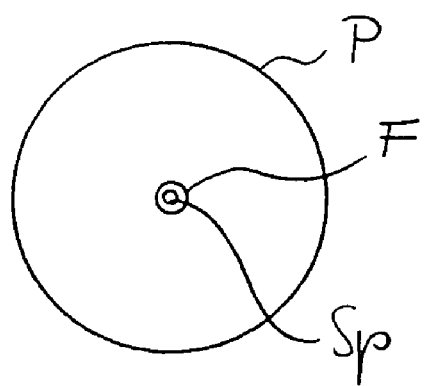
Figure 4:
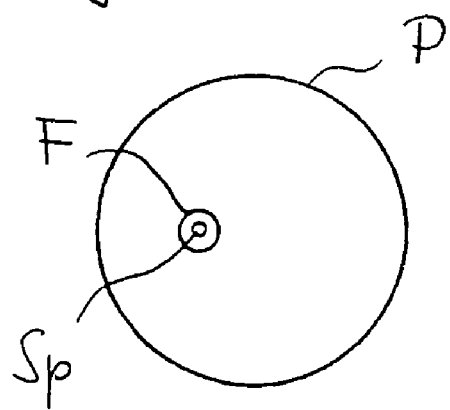

This is shown diagrammatically in FIGS. 2, 3 and 4. These figures each show the superimposed images mentioned.

FIG. 2 shows the rim P of the pupil, the fovea F and the fixation light spot Sp, such as are obtained with the aid of an above described superimposed image of the two cameras 36 and 40 in the computer 38 and can, optionally, be displayed on a suitable viewing screen. In the situation in accordance with FIG. 2, the patient does not fixate the fixation light source correctly. The physician detects this from the fact that the fixation light spot Sp is not precisely in the fovea F but is offset with respect to it. This has the consequence that the physician has to take appropriate measures to induce the patient to make a precise fixation.

FIG. 3 shows the ideal case, in which the patient fixates precisely and consequently the fixation light spot Sp is situated precisely concentrically with the fovea F. With the finding in accordance with FIG. 3, the fovea F is also central in the pupil P. This does not always have to be the case. FIG. 4 shows an example in which, although the patient correctly fixates the fixation light source 22 so that the fixation light spot Sp is situated precisely in the fovea F, the fovea F is not central in the pupil P. Still more complicated findings are possible in which the pupil rim shown does not at all have the ideal circular shape shown in the figures, but deviates from it. This applies, in particular, after ophthalmological operations already performed earlier.

In the case of a finding in accordance with FIG. 4, the position of fixation light spot Sp and fovea F found to be eccentric with respect to the pupil P can be chosen as ablation centre, i.e. the ablation takes place in a centred manner with respect to the central point of Sp and F. This option has also given good results.

The invention claimed is:

1. An ophthalmological apparatus, comprising:
a laser for providing a laser beam for treating a cornea of an eye of a patient;
a fixation light source for emitting a fixation light beam at a visible wavelength, the fixation light beam provided for visual fixation by the patient;
a first camera adapted for focusing on a retinal plane of the eye to capture a first image showing a retinal area including a fovea of the eye, wherein the first camera is positioned to receive a portion of the fixation light beam reflected from the retina of the eye so that the first image includes a visible light spot generated by the fixation light beam on the retina;
a computer performing an evaluation function for determining from the first image whether the light spot is sufficiently precise on the fovea to determine if the patient properly fixates the fixation light beam with the eye;
a second camera focused on a plane of a pupil of the eye for capturing a second image showing the pupil;
wherein the computer performs a superimposing function for superimposing the first and second images to allow a determination of a positional relationship of the light spot and fovea with respect to the pupil.

2. An ophthalmological apparatus, comprising:
a laser for providing a laser beam for treating a cornea of an eye of a patient;
a fixation light source for emitting a fixation light beam at a visible wavelength, the fixation light beam provided for visual fixation by the patient;
a first camera adapted for focusing on a retinal plane of the eye to capture a first image showing a retinal area including a fovea of the eye, wherein the first camera is positioned to receive a portion of the fixation light beam reflected from the retina of the eye so that the first image includes a visible light spot generated by the fixation light beam on the retina;
a computer performing an evaluation function for determining from the first image whether the light spot is sufficiently precise on the fovea to determine if the patient properly fixates the fixation light beam with the eye;
wherein the first camera is adapted to zoom between the retinal plane and a pupil plane of the eye to selectively capture the first image and a second image showing the pupil base based on a zooming state of the first camera.

3. The apparatus according to claim 2, wherein the computer performs a superimposing function for superimposing the first and second images to allow a determination of a positional relationship of the light spot and fovea with respect to the pupil.

4. An ophthalmological apparatus, comprising:
a laser for providing a laser beam for treating a cornea of an eye of a patient;
a fixation light source for emitting a fixation light beam at a visible wavelength, the fixation light beam provided for visual fixation by the patient;
a first camera adapted for focusing on a retinal plane of the eye to capture a first image showing a retinal area including a fovea of the eye, wherein the first camera is positioned to receive a portion of the fixation light beam reflected from the retina of the eye so that the first image includes a visible light spot generated by the fixation light beam on the retina;
a computer performing an evaluation function for determining from the first image whether the light spot is sufficiently precise on the fovea to determine if the patient properly fixates the fixation light beam with the eye and performing an image processing function for processing the first image to calculate an ablation center as a center point of the light spot and the fovea; and
a control unit for controlling the laser such as to move the laser beam across a cornea of the eye in a centered manner with respect to the calculated ablation center.

5. An ophthalmological method, comprising:
providing a laser beam for treating a cornea of an eye of a patient;
emitting a fixation light beam at a visible wavelength, the fixation light beam provided for visual fixation by the patient;
capturing, by using a first camera focused on a retinal plane of the eye, a first image showing a retinal area including a fovea of the eye, the first image including a visible light spot generated by the fixation light beam on the retina;
determining from the first image whether the light spot is sufficiently precise on the fovea to determine if the patient properly fixates the fixation light beam with the eye;
capturing, by using a second camera focused on a plane of a pupil of the eye, a second image showing the pupil; and
superimposing the first and second images to allow a determination of a positional relationship of the light spot and fovea with respect to the pupil.

6. An ophthalmological method, comprising:
providing a laser beam for treating a cornea of an eye of a patient;
emitting a fixation light beam at a visible wavelength, the fixation light beam provided for visual fixation by the patient;
capturing, by using a first camera focused on a retinal plane of the eye, a first image showing a retinal area including a fovea of the eye, the first image including a visible light spot generated by the fixation light beam on the retina;
determining from the first image whether the light spot is sufficiently precise on the fovea to determine if the patient properly fixates the fixation light beam with the eye;
zooming the first camera between the retinal plane and a pupil plane of the eye to selectively capture the first image and a second image showing the pupil based on a zooming state of the first camera.

7. The method according to claim 6, further comprising:
superimposing the first and second images to allow a determination of a positional relationship of the light spot and fovea with respect to the pupil.

8. An ophthalmological method, comprising:
providing a laser beam for treating a cornea of an eye of a patient;
emitting a fixation light beam at a visible wavelength, the fixation light beam provided for visual fixation by the patient;
capturing, by using a first camera focused on a retinal plane of the eye, a first image showing a retinal area including a fovea of the eye, the first image including a visible light spot generated by the fixation light beam on the retina;
determining from the first image whether the light spot is sufficiently precise on the fovea to determine if the patient properly fixates the fixation light beam with the eye;
processing the first image to calculate an ablation center as a center point of the light spot and the fovea; and
controlling the laser such as to move the laser beam across a cornea of the eye in a centered manner with respect to the calculated ablation center.

* * * * *